(12) United States Patent
Park et al.

(10) Patent No.: US 10,214,598 B2
(45) Date of Patent: Feb. 26, 2019

(54) (METH)ACRYLATE COMPOUND, AND COPOLYMER AND HOMOPOLYMER COMPRISING REPEATING UNIT DERIVED FROM SAME

(71) Applicant: LG CHEM, LTD., Seoul (KR)

(72) Inventors: Kwang Seung Park, Daejeon (KR); Mi Rin Lee, Daejeon (KR); Jun Wuk Park, Daejeon (KR); Eunsoo Huh, Daejeon (KR); Sung Hyun Jeon, Daejeon (KR)

(73) Assignee: LG CHEM, LTD., Seoul (KR)

( * ) Notice: Subject to any disclaimer, the term of this patent is extended or adjusted under 35 U.S.C. 154(b) by 32 days.

(21) Appl. No.: 15/508,809

(22) PCT Filed: Sep. 25, 2015

(86) PCT No.: PCT/KR2015/010210
§ 371 (c)(1),
(2) Date: Mar. 3, 2017

(87) PCT Pub. No.: WO2016/052953
PCT Pub. Date: Apr. 7, 2016

(65) Prior Publication Data
US 2017/0275397 A1    Sep. 28, 2017

(30) Foreign Application Priority Data

Sep. 30, 2014 (KR) .................. 10-2014-0132135

(51) Int. Cl.
| | | |
|---|---|---|
| *C08F 20/06* | (2006.01) | |
| *C08F 22/36* | (2006.01) | |
| *C07C 57/04* | (2006.01) | |
| *C07D 203/08* | (2006.01) | |
| *C07C 275/04* | (2006.01) | |
| *C07C 219/08* | (2006.01) | |
| *C08L 33/04* | (2006.01) | |
| *C07C 275/10* | (2006.01) | |
| *C07C 57/13* | (2006.01) | |
| *C08F 18/04* | (2006.01) | |
| *C08F 22/10* | (2006.01) | |

(52) U.S. Cl.
CPC .............. *C08F 20/06* (2013.01); *C07C 57/04* (2013.01); *C07C 219/08* (2013.01); *C07C 275/04* (2013.01); *C07C 275/10* (2013.01); *C07D 203/08* (2013.01); *C08F 22/36* (2013.01); *C08L 33/04* (2013.01); *C07C 57/13* (2013.01); *C08F 18/04* (2013.01); *C08F 22/105* (2013.01)

(58) Field of Classification Search
CPC ........ C08F 20/06; C08F 22/36; C07D 203/08; C07C 57/04; C07C 57/13
See application file for complete search history.

(56) References Cited

U.S. PATENT DOCUMENTS

| | | | |
|---|---|---|---|
| 6,943,211 B1 | 9/2005 | Hubbell et al. | |
| 7,652,103 B2 * | 1/2010 | Kavanagh | C08F 220/00 156/325 |
| 7,714,076 B2 * | 5/2010 | Krepski | C09J 133/064 156/325 |
| 7,838,110 B2 * | 11/2010 | Zhu | C07D 203/08 428/345 |
| 2010/0167200 A1 | 7/2010 | Choi et al. | |
| 2015/0073171 A1 | 3/2015 | Breiner et al. | |

FOREIGN PATENT DOCUMENTS

| | | |
|---|---|---|
| JP | 1974-02434 A | 2/1974 |
| JP | 2014-174235 A | 9/2014 |
| KR | 10-2010-0080146 A | 7/2010 |
| WO | 2013/131818 A1 | 9/2013 |

* cited by examiner

*Primary Examiner* — Robert D. Harlan
(74) *Attorney, Agent, or Firm* — Dentons US LLP

(57) ABSTRACT

The present specification relates to a (meth)acrylate compound, and a copolymer and a homopolymer including a repeating unit derived therefrom.

13 Claims, 2 Drawing Sheets

[Figure 1]
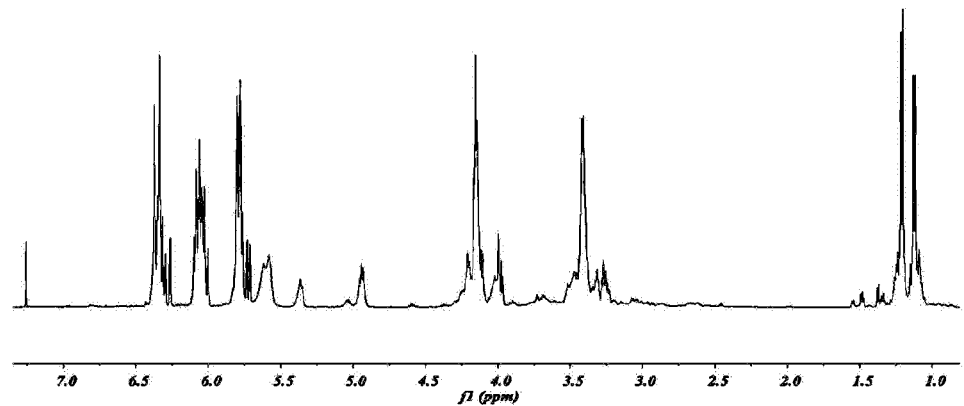
[Figure 2]
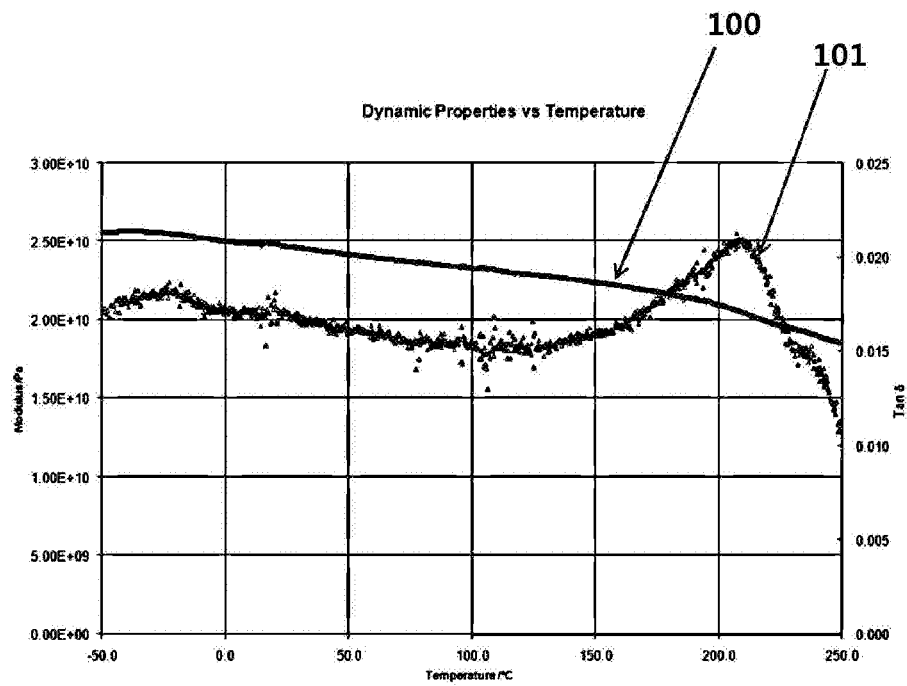

[Figure 3]
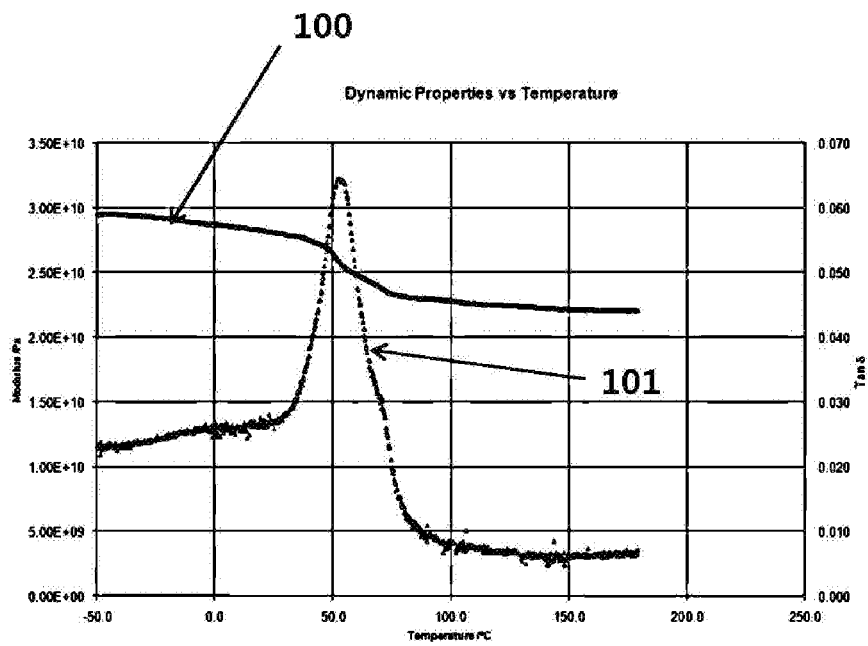
[Figure 4]
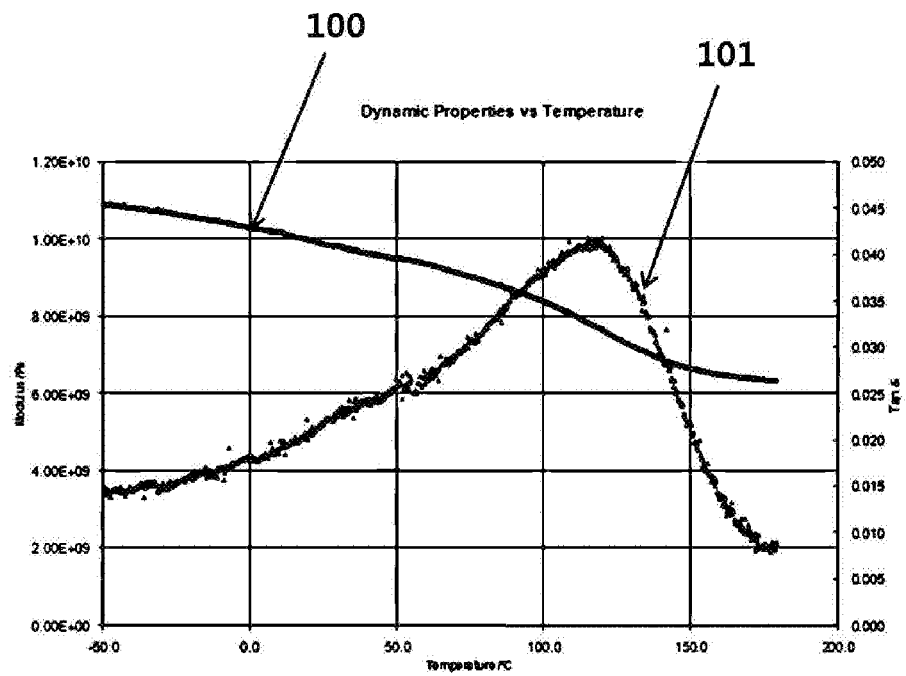

(METH)ACRYLATE COMPOUND, AND COPOLYMER AND HOMOPOLYMER COMPRISING REPEATING UNIT DERIVED FROM SAME

This application is a National Stage Entry of International Application No. PCT/KR2015/010210, filed on Sep. 25, 2015, and claims the benefit of and priority to Korean Application No. 10-2014-0132135, filed on Sep. 30, 2014, all of which are hereby incorporated by reference in their entirety for all purposes as if fully set forth herein.

TECHNICAL FIELD

The present specification relates to a (meth)acrylate compound, and a copolymer and a homopolymer including a repeating unit derived therefrom.

BACKGROUND ART

A polarizing plate has been generally used for durability and water resistance as a structure where a protection film is laminated on one surface or both surfaces of a polarizer formed of a polyvinyl alcohol (hereinafter, referred to as 'PVA')-based resin generally dyed with a dichromatic dye or iodine by using an adhesive. In this case, as the adhesive used to attach the polarizer and the protection film, an aqueous adhesive formed of an aqueous solution of a polyvinyl alcohol-based resin has been mostly used. However, there is a problem in that adhesive strength of the aqueous adhesive is reduced according to a kind of material of the film, and in order to overcome this, a method of using a non-aqueous adhesive has been proposed. In this case, the non-aqueous adhesive may be divided into a heat-curable adhesive and a UV-curable adhesive.

Further, recently, for reduction in thickness and weight, a technology of applying a curable composition on one surface or both surfaces of the polarizer to form a transparent thin film layer has been proposed. In this case, the protection film is provided on one surface of the polarizer and the transparent thin film layer may be formed on an opposite surface thereto.

As described above, in the case of the adhesive composition or the composition forming the transparent thin film layer, in common, the UV-curable composition may be used. The UV-curable composition is a very useful material due to convenient workability and rapid curability in a process of manufacturing the polarizing plate. Meanwhile, in the related art, as the UV-curable composition, an acryl-based polymer or a methacryl-based polymer has been used. However, this UV-curable composition has a merit in terms of convenience due to a rapid curing speed, but there is a drawback in that due to this characteristic, as compared to thermosetting polymers and thermoplastic polymers, since a reaction is not performed for a sufficient time, a molecular weight is not relatively sufficiently increased, and thus it is difficult to embody a high modulus of elasticity and a high glass transition temperature.

Therefore, in order to overcome this drawback, there is a demand for a novel compound (monomer) providing a polymer which can embody a high storage modulus and a high glass transition temperature as compared to the UV-curable composition in the related art.

DETAILED DESCRIPTION OF THE INVENTION

Technical Problem

The present specification has been made in an effort to provide a (meth)acrylate compound, and a copolymer and a homopolymer including a repeating unit derived therefrom.

Technical Solution

According to an exemplary embodiment of the present specification, there is provided a (meth)acrylate compound represented by the following Chemical Formula 1.

[Chemical Formula 1]

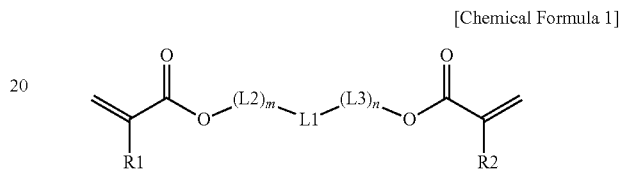

In Chemical Formula 1,
at least one of R1 and R2 is hydrogen and a remainder is an alkyl group having 1 to 10 carbon atoms,
L1 is —N(H)C(=O)N(H)—; or —N(H)C(=O)-L4-C(=O)N(H)—,
L2 to L4 are the same as or different from each other, and are each independently an alkylene group having 1 to 10 carbon atoms unsubstituted or substituted by an alkyl group,
in the case where L2 and L3 are the same as or different from each other and are each independently an unsubstituted alkylene group having 1 to 10 carbon atoms, one of R1 and R2 is an alkyl group having 1 to 10 carbon atoms,
m and n are each 1 or 2, and
in the case where m and n are each 2, structures in two brackets are the same as or different from each other.

According to the exemplary embodiment of the present specification, there is provided a copolymer including: a repeating unit derived from the (meth)acrylate compound represented by Chemical Formula 1.

Further, according to the exemplary embodiment of the present specification, there is provided a homopolymer including: a repeating unit derived from the (meth)acrylate compound represented by Chemical Formula 1.

Advantageous Effects

A (meth)acrylate compound according to an exemplary embodiment of the present specification has a merit in that a glass transition temperature as well as a storage modulus of a polymer obtained by UV curing may be significantly improved.

Further, the (meth)acrylate compound may be included in a UV-curable composition, the UV-curable composition including the (meth)acrylate compound may be used to form an adhesive or a protection film of a polarizing plate and has excellent heat resistance and durability.

BRIEF DESCRIPTION OF DRAWINGS

FIG. 1 is a $^1$H NMR spectrum of Chemical Formula 1-4 manufactured through Synthesis Example 1.

FIG. 2 is a measurement graph of a glass transition temperature of Chemical Formula 1-4 of Experimental Example 1.

FIG. 3 is a measurement graph of a glass transition temperature of AOPI of Comparative Example 3.

FIG. 4 is a measurement graph of a glass transition temperature of Chemical Formula 7 of Comparative Example 4.

EXPLANATION OF REFERENCE NUMERALS AND SYMBOLS

100: Modulus
101: Tan Delta ps [BEST MODE]

Hereinafter, the present specification will be described in more detail. However, the exemplary embodiments of the present specification may be modified into various other forms and the scope of the present specification is not limited to exemplary embodiments as will be described below. Further, the exemplary embodiments of the present specification are provided so that those skilled in the art may completely understand the present specification.

According to an exemplary embodiment of the present specification, there is provided a (meth)acrylate compound represented by Chemical Formula 1.

While the present inventors developed a UV-curable polymer having a storage modulus of 3000 MPa or more, the present inventors developed a (meth)acrylate compound having a novel structure manufactured by reacting a compound including an aziridine group in a molecule thereof, and (meth)acrylate including an acrylic acid, a (meth)acrylic acid, or a hydroxy group (—OH) as a substituent group, and found that by using this compound, a polymer resin having a high storage modulus and a high glass transition temperature can be manufactured, thereby accomplishing the present invention.

In the present specification, the term "substituted" means that a hydrogen atom bonded to a carbon atom of a compound is changed into another substituent group, a substitution position is not limited as long as the substitution position is a position at which the hydrogen atom is substituted, that is, a position at which the substituent group can be substituted, and in the case where two or more atoms are substituted, two or more substituent groups may be the same as or different from each other.

In the present specification, the alkyl group may be a straight or branched chain, and the number of carbon atoms thereof is not particularly limited but is preferably 1 to 30. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, the alkylene group means a group where two bonding positions exist at the alkyl group, that is, a divalent group. Except that the groups are each the divalent group, the aforementioned description of the alkyl group may be applied.

According to the exemplary embodiment of the present specification, in Chemical Formula 1, at least one of R1 and R2 is hydrogen, and the remainder is a methyl group.

According to the exemplary embodiment of the present specification, in Chemical Formula 1, R1 and R2 are hydrogen.

According to the exemplary embodiment of the present specification, in Chemical Formula 1, R1 is hydrogen, and R2 is a methyl group.

According to the exemplary embodiment of the present specification, in Chemical Formula 1, R2 is hydrogen, and R1 is a methyl group.

According to the exemplary embodiment of the present specification, in Chemical Formula 1, L1 is —N(H)C(=O)N(H)—.

According to the exemplary embodiment of the present specification, in Chemical Formula 1, L2 and L3 are the same as or different from each other, and are each independently an alkylene group having 1 to 10 carbon atoms unsubstituted or substituted by a methyl group.

According to the exemplary embodiment of the present specification, in Chemical Formula 1, L2 and L3 are the same as or different from each other, and are each independently an ethylene group; or an ethylene group substituted by a methyl group.

According to the exemplary embodiment of the present specification, in Chemical Formula 1, L2 and L3 are an ethylene group.

According to the exemplary embodiment of the present specification, in Chemical Formula 1, L2 is an ethylene group, and L3 is an ethylene group substituted by a methyl group.

According to the exemplary embodiment of the present specification, in Chemical Formula 1, L3 is an ethylene group, and L2 is an ethylene group substituted by a methyl group.

According to the exemplary embodiment of the present specification, in Chemical Formula 1, in the case where L2 and L3 are the same as or different from each other and are each independently an unsubstituted alkylene group having 1 to 10 carbon atoms, one of R1 and R2 is an alkyl group having 1 to 10 carbon atoms.

According to the exemplary embodiment of the present specification, in Chemical Formula 1, in the case where L2 and L3 are the same as or different from each other and are each independently an unsubstituted ethylene group, one of R1 and R2 is a methyl group.

The (meth)acrylate compound represented by Chemical Formula 1 according to the exemplary embodiment of the present specification is obtained by a reaction of an aziridine compound; and acrylate including a (meth)acrylic acid or a hydroxy group (—OH) as a substituent group.

The (meth)acrylate compound represented by Chemical Formula 1 has a structure formed by a ring-opening reaction between the aziridine compound, and (meth)acrylate including the (meth)acrylic acid or the hydroxy group (—OH) as the substituent group. In this case, an amine group in the compound serves to improve a glass transition temperature and a storage modulus of the polymer obtained by UV curing, and the acrylate group or the (meth)acrylate group at an end thereof serves as a reaction group by ultraviolet rays.

The aziridine compound is a compound including at least one aziridine group, and the number of the aziridine groups or the structure and the number of substituent groups attached to the aziridine groups are not limited, but for example, the aziridine compound is represented by the following Chemical Formula 2 or 3.

[Chemical Formula 2]

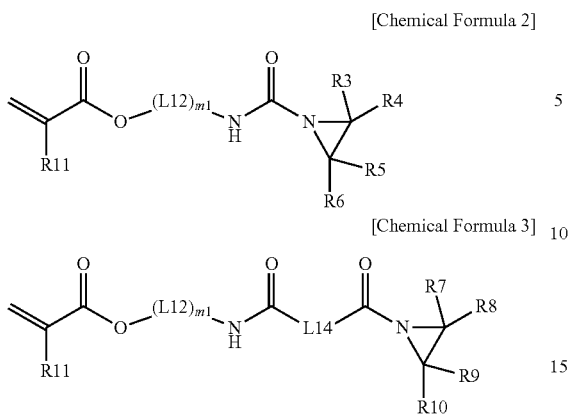

[Chemical Formula 3]

[Chemical Formula 1-1]

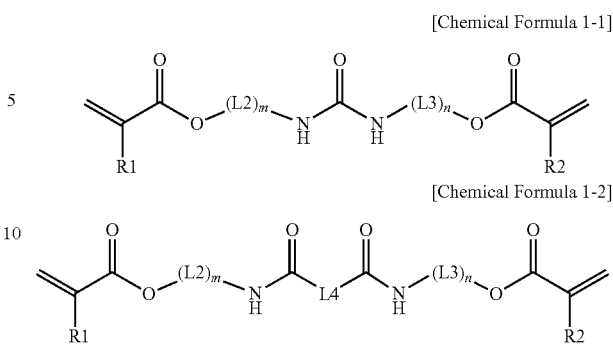

[Chemical Formula 1-2]

In Chemical Formulas 1-1 and 1-2,
definitions of R1, R2, L2 to L4, m, and n are the same as those of Chemical Formula 1.

According to the exemplary embodiment of the present specification, the (meth)acrylate compound represented by Chemical Formula 1 is represented by the following Chemical Formulas 1-3 to 1-5.

[Chemical Formula 1-3]

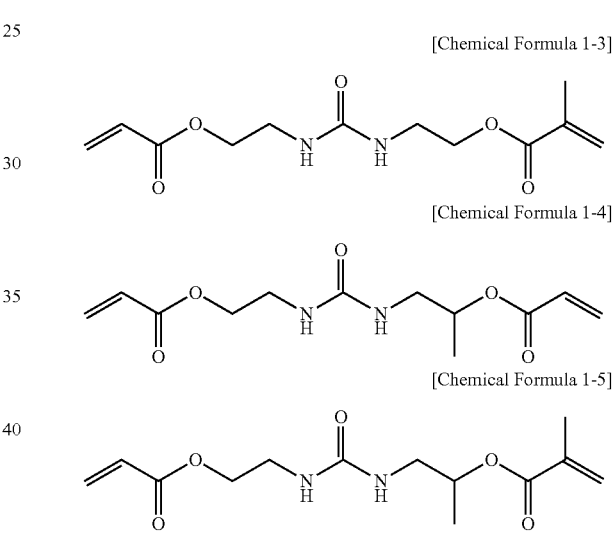

[Chemical Formula 1-4]

[Chemical Formula 1-5]

In Chemical Formulas 2 and 3,

R3 to R11 are the same as or different from each other, and are each independently hydrogen; or an alkyl group having 1 to 10 carbon atoms, L12 and L14 are the same as or different from each other, and are each independently an alkylene group having 1 to 10 carbon atoms unsubstituted or substituted by an alkyl group, m1 is 1 or 2, and in the case where m1 is 2, two L12s are the same as or different from each other.

In the present specification, the (meth)acrylic acid means the acrylic acid or the methacrylic acid.

In the present specification, (meth)acrylate means acrylate or methacrylate.

According to the exemplary embodiment of the present specification, (meth)acrylate including the hydroxy group (—OH) as the substituent group is represented by the following Chemical Formula 4.

[Chemical Formula 4]

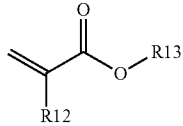

In Chemical Formula 4,

R12 is hydrogen; or an alkyl group having 1 to 10 carbon atoms, and

R13 is an alkyl group having 1 to 10 carbon atoms substituted by at least one hydroxy group (—OH); or a cycloalkyl group having 3 to 10 carbon atoms substituted by at least one hydroxy group (—OH).

In the present specification, a cycloalkyl group is not particularly limited, but the number of carbon atoms thereof is preferably 3 to 30, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

According to the exemplary embodiment of the present specification, the (meth)acrylate compound represented by Chemical Formula 1 is represented by the following Chemical Formula 1-1 or 1-2.

In the (meth)acrylate compound represented by Chemical Formula 1, an amine group (—NH—) positioned in the middle of a chain of the compound forms a hydrogen bond together with an amine group (—NH—) formed in a chain of another compound to reinforce binding among polymer chains, and thus a glass transition temperature and a storage modulus are increased.

Meanwhile, hereinafter, a method of manufacturing the (meth)acrylate compound of the present invention will be described.

The manufacturing method of the present invention is performed by the ring-opening reaction between aziridine and the (meth)acrylic acid, and synthesis may be easily performed due to strong reactivity of aziridine. In this case, the reaction may be performed preferably at about 30° C. to 80° C., because in the case where the aforementioned range is satisfied, synthesis may be easily performed without the occurrence of gelling of the (meth)acrylic acid.

Meanwhile, it is preferable that the reaction is performed so that a content ratio between a monomer including the aziridine group and a (meth)acrylic acid monomer is an equivalent ratio of about 1:1, or in order to react all aziridine groups, the equivalent of the acrylic acid within 5% is further added to perform the reaction. That is, it is preferable that in the (meth)acrylate compound of the present specification, all aziridine groups existing at an end of the aziridine compound of a reactant are reacted with the (meth)acrylic acid. The reason is that in the case where the aziridine group remains in the generated (meth)acrylate compound, physical properties such as the glass transition temperature may be reduced.

To be more specific, it is preferable that a mole ratio of the aziridine compound represented by Chemical Formula 2 or 3 and (meth)acrylate including the (meth)acrylic acid or the hydroxy group (—OH) represented by Chemical Formula 4 as the substituent group is 1:1.

According to another exemplary embodiment of the present invention, there is provided a polymer including a repeating unit derived from the (meth)acrylate compound. That is, there is provided the polymer which is obtained by a reaction of the aziridine compound; and (meth)acrylate including the (meth)acrylic acid or the hydroxy group (—OH) as the substituent group and includes the repeating unit derived from the (meth)acrylate compound represented by Chemical Formula 1.

In this case, the polymer may be a copolymer obtained by a copolymer between the (meth)acrylate compound according to the present specification and another monomer, and in the copolymer, a bonding type of the polymers is not limited regardless of the kind and the number of repeating units, that is, the copolymer may be a block copolymer type were the repeating units are repeated, or a random copolymer type where the repeating units are randomly repeated. Further, it is preferable that the polymer, in views of an increase in the glass transition temperature and the storage modulus, is a homopolymer including only the repeating unit derived from the (meth)acrylate compound. In the case where the polymer is the homopolymer, since a density of a hydrogen bond by the amine group is higher, binding among the polymer chains may be reinforced, and thus the glass transition temperature and the storage modulus are more excellent.

Generally, the more the number of functional groups of the polymer used as a UV-curable type is, the higher the storage modulus is. Nevertheless, it is difficult to obtain the storage modulus of more than 3000 MPa. However, the polymer including the aziridine reaction group may have the storage modulus at a level that is higher than that of a UV cured material having a general structure. However, there are problems in that in the case where the polymer has only the aziridine reaction group, UV curing does not occur, and even in the case where in the polymer, UV-polymerization reaction groups such as the aziridine group and the (meth)acrylate group coexist, physical properties of the polymer are hindered because the glass transition temperature is low.

In order to compensate for these drawbacks, in the case where in the compound including the aziridine group, the aziridine group and (meth)acrylate including the (meth) acrylic acid or the hydroxy group (—OH) as the substituent group at the same equivalent ratio are reacted to manufacture the (meth)acrylate compound having the novel structure and the homopolymer is formed by using the (meth)acrylate compound, the physical property that is identical with or higher than the storage modulus of the homopolymer is expressed, and simultaneously, the glass transition temperature is significantly improved. This is that the amine group positioned in the middle of the chain of the homopolymer forms the hydrogen bond together with the amine group of another chain to reinforce binding among the chains.

To be more specific, according to the exemplary embodiment of the present specification, the homopolymer including the repeating unit derived from the (meth)acrylate compound represented by Chemical Formula 1 is characterized in that the glass transition temperature is 100° C. to 300° C. The glass transition temperature may be preferably about 100° C. to 200° C., and more preferably 150° C. to 200° C. In the case where the glass transition temperature satisfies the aforementioned range, the polymer having excellent mechanical properties such as heat resistance and dimensional stability may be embodied.

Further, according to the exemplary embodiment of the present specification, the homopolymer including the repeating unit derived from the (meth)acrylate compound represented by Chemical Formula 1 is characterized in that the storage modulus measured by a DMA (dynamic mechanical analysis) method at 25° C. is 3000 MPa to 30000 MPa, and preferably about 3000 MPa to 10000 MPa. In the case where the storage modulus satisfies the aforementioned range, the polymer having excellent mechanical properties such as heat resistance and dimensional stability may be embodied.

According to the exemplary embodiment of the present specification, a gel fraction of the homopolymer including the repeating unit derived from the (meth)acrylate compound represented by Chemical Formula 1 may be calculated by the following General Formula 1 and is 85% to 100%, and in the case where the gel fraction satisfies the aforementioned range, chemical resistance is excellent.

Gel fraction (%)=$B/A$×100     [General Formula 1]

In General Formula 1,

A is a mass of a mixture obtained by polymerizing the repeating units derived from the (meth)acrylate compound represented by Chemical Formula 1, and B represents a dry mass of an insoluble portion sampled after A is deposited in methylethylketone at normal temperature for 72 hours.

A is the mass of the mixture of the repeating unit, the oliogomer, and the homopolymer derived from the (meth) acrylate compound represented by Chemical Formula 1, and B is the mass of the homopolymer including the repeating unit derived from the (meth)acrylate compound represented by Chemical Formula 1.

Polymerization of the homopolymer according to the exemplary embodiment of the present specification may be confirmed through calculation of the gel fraction of General Formula 1.

According to the exemplary embodiment of the present specification, in an IR spectrum of the homopolymer including the repeating unit derived from the (meth)acrylate compound represented by Chemical Formula 1, a peak of a region band of 1408 cm$^{-1}$ which is a C=C band of (meth) acrylate of the repeating unit derived from the (meth) acrylate compound of the homopolymer is reduced as compared to that of an IR spectrum of the (meth)acrylate compound. It can be confirmed that as the peak of the region band of 1408 cm$^{-1}$ is reduced, a C=C bond of the (meth) acrylate group at an end of the repeating unit derived from the (meth)acrylate compound represented by Chemical Formula 1, and another C=C bond of (meth)acrylate at the end of the repeating unit derived from the (meth)acrylate compound represented by Chemical Formula 1 tend to be reacted to perform polymerization, and in this case, the glass transition temperature and film strength of the homopolymer are increased.

The IR spectrum of the homopolymer means that an integral value of peak areas of the region band of 1408 cm$^{-1}$ which is the C=C band of the (meth)acrylate group of the repeating unit derived from the (meth)acrylate compound of the homopolymer is reduced by 80% or more based on 100% of an integral value of peak areas of the IR spectrum of the (meth)acrylate compound. More preferably, the integral value is reduced by 80 to 100%. In this case, it can be confirmed that the C=C bond of the (meth)acrylate group at the end of the repeating unit derived from the (meth)acrylate compound represented by Chemical Formula 1, and another C=C bond of (meth)acrylate at the end of the repeating unit derived from the (meth)acrylate compound represented by Chemical Formula 1 tend to be reacted to perform polymerization, and in this case, the glass transition temperature and film strength of the homopolymer are increased.

The IR spectrum of the (meth)acrylate compound means the IR spectrum of the (meth)acrylate compound represented by Chemical Formula 1.

photoinitiator such as Irgacure 819 (Ciba Company) was uniformly dissolved and mixed in the content of 0.5 to 5 parts by weight based on 100 parts by weight of the total mixing content, the layer of the resulting mixture was formed in the thickness of 1 to 20 µm on the transparent film such as the release PET film, and ultraviolet rays of 200 mJ/cm² or more were irradiated through the metal-halide type UV lamp to manufacture the polymer.

Polymerization of the synthesized homopolymer was confirmed through calculation of the gel fraction of General Formula 1 and IR analysis.

COMPARATIVE EXAMPLE 1

As the control group of the aforementioned Synthesis Example, bisphenol A type epoxy acrylate (Cytec Industries, EB600, the following Chemical Formula 5) that was the (meth)acrylate compound used in the related art was used.

[Chemical Formula 5]

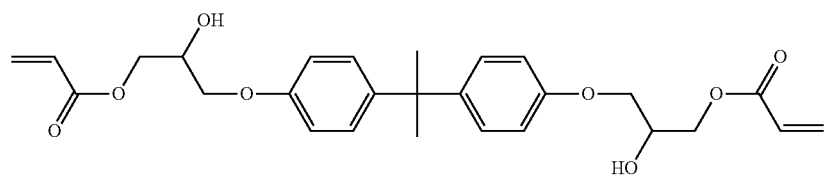

Hereinafter, the present specification will be described in more detail through the Examples. The following Examples are set forth to help understanding of the present specification, but are not to be construed to limit the present specification.

SYNTHESIS EXAMPLE 1

After 19.8 g of 2-(2-methylaziridine-1-carboxamido)ethyl acrylate (AK ChemTech, Co., Ltd., AOPI, purity of 95% or more) was agitated and the temperature thereof was increased to about 60° C., 7.5 g of the acrylic acid (Aldrich Corporation) was slowly added through the syringe for 10 minutes to perform the reaction at about 60° C. for about 6 hours. Thereafter, the process of increasing the purity was performed through the column purification method to synthesize the compound of Chemical Formula 1-4.

The following FIG. 1 is a ¹H NMR spectrum of Chemical Formula 1-4 manufactured through Synthesis Example 1.

SYNTHESIS EXAMPLE 2

The compound of Chemical Formula 1-5 was synthesized through the same method as Synthesis Example 1, except that as the aziridine compound, instead of trimethylolpropane-tris-(β-N-aziridinyl) propionate (MENADIONA, S.L., CL-422), 19.8 g of 2-(2-methylaziridine-1-carboxamido) ethyl acrylate (AK ChemTech, Co., Ltd., AOPI, purity of 95% or more) and 9.0 g of the methacrylic acid were used.

SYNTHESIS EXAMPLE 3

Manufacturing of Homopolymer

Chemical Formulas 1-4 and 1-5 synthesized in Synthesis Examples 1 and 2 were alone used or mixed, and the radical

COMPARATIVE EXAMPLE 2

As the control group of the aforementioned Synthesis Example, 2-(methacryloyloxy)ethyl dihydrogen phosphate (Cytec Industries, HS-100, the following Chemical Formula 6) as the (meth)acrylate compound used in the related art was used.

[Chemical Formula 6]

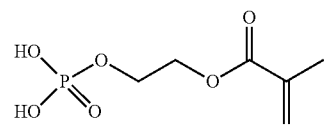

COMPARATIVE EXAMPLE 3

As the control group of the aforementioned Synthesis Example, 2-(2-methylaziridine-1-carboxamido)ethyl acrylate (AK ChemTech, Co., Ltd., AOPI, purity of 95% or more) that was the pure aziridine compound was used.

COMPARATIVE EXAMPLE 4

As the control group of the aforementioned Synthesis Example, the following Chemical Formula 7 that was the (meth)acrylate compound was used.

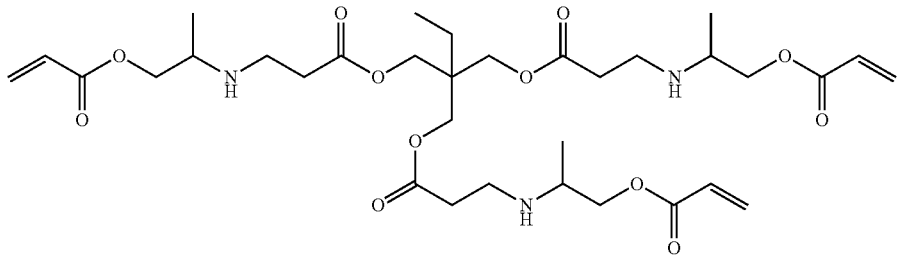

[Chemical Formula 7]

EXPERIMENTAL EXAMPLE

Physical properties of the compound of Chemical Formula 1-4 manufactured through Synthesis Example 1 and the compound disclosed in Comparative Examples 1 to 4 were measured by the following method, and the results are described in the following Table 1.

1. Storage Modulus and Glass Transition Temperature After Curing

In order to measure the storage modulus after curing of Chemical Formula 1-4 (Example 1) that was the manufactured (meth)acrylate compound and the control group compounds (Comparative Examples 1 to 4), the Irgacure 819 photoinitiator (Ciba Company) was uniformly mixed at 60° C. in the content of 3 parts by weight based on 100 parts by weight of the corresponding sample, followed by curing with energy of 1000 mJ/cm$^2$ between the release films through the D bulb curing machine manufactured by Fusion Company. Thereafter, the aforementioned cured material was cut in the size of the width of 5.3 mm and the length of 50 mm to actually measure the thickness, and by using DMA (TA Instruments), the temperature was increased to −40° C. to 160° C. to measure the storage modulus and the glass transition temperature. Among them, the result of the storage modulus at 25° C. is described in the following Table 1.

FIG. 2 is a measurement graph of a glass transition temperature of Chemical Formula 1-4 of Experimental Example 1.

FIG. 3 is a measurement graph of a glass transition temperature of AOPI of Comparative Example 3.

FIG. 4 is a measurement graph of a glass transition temperature of Chemical Formula 7 of Comparative Example 4.

In the following Table 1 and the graphs of FIGS. 2 to 4, it can be seen that the (meth)acrylate compound having two (meth)acrylates according to the exemplary embodiment of the present specification has the glass transition temperature which is higher than that of the compound having one or three (meth)acrylate groups.

Although the exemplary embodiments of the present specification are described in detail, the scope of the right of the present specification is not limited to the exemplary embodiments, and it will be apparent to those skilled in the art that various modifications and changes may be made thereto without departing from the technical spirit of the present specification described in the claims.

The invention claimed is:

1. A (meth)acrylate compound represented by the following Chemical Formula 1:

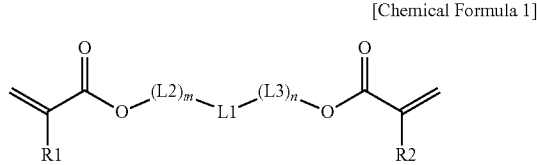

[Chemical Formula 1]

in Chemical Formula 1,
at least one of R1 and R2 is hydrogen and a remainder is an alkyl group having 1 to 10 carbon atoms,
L1 is —N(H)C(=O)N(H)—; or —N(H)C(=O)-L4-C(=O)N(H)—,
L2 to L4 are the same as or different from each other, and are each independently an alkylene group having 1 to 10 carbon atoms unsubstituted or substituted by an alkyl group,
in the case where L2 and L3 are the same as or different from each other and are each independently an unsubstituted alkylene group having 1 to 10 carbon atoms, one of R1 and R2 is an alkyl group having 1 to 10 carbon atoms,
m and n are each 1 or 2,
when m is 2, two L2s are the same as or different from each other, and

TABLE 1

| Classification | Aziridine compound | Acid | Generated (meth)acrylate compound | Storage modulus (MPa) | Glass transition temperature (° C.) |
|---|---|---|---|---|---|
| Experimental Example 1 | AOPI | Acrylic acid | Chemical Formula 1-4 | 4700~4900 | 210 |
| Comparative Example 1 | | | Biphenol A type epoxy acrylate, | 1400~1600 | 87 |
| Comparative Example 2 | | | 2-(methacryloyloxy)ethyl dihydrogen phosphate | 700~900 | 15 |
| Comparative Example 3 | | | AOPI | 1700~1900 | 52 |
| Comparative Example 4 | | | Chemical Formula 7 | 4100~4300 | 117 | when n is 2, two L3s are the same as or different from each other.

2. The (meth)acrylate compound of claim 1, wherein Chemical Formula 1 is obtained by a reaction of an aziridine compound and a (meth)acrylic acid; or by a reaction of an aziridine compound and a hydroxyalkyl (meth)acrylate or a hydroxycycloalkyl (meth)acrylate.

3. The (meth)acrylate compound of claim 2, wherein the aziridine compound is represented by the following Chemical Formula 2 or 3:

[Chemical Formula 2]

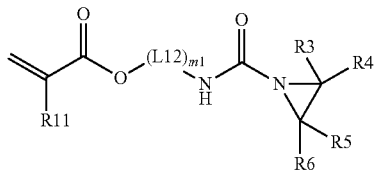

[Chemical Formula 3]

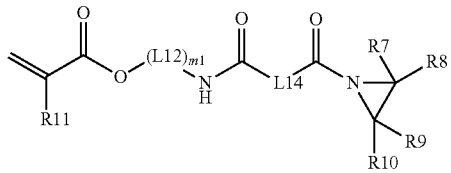

in Chemical Formulas 2 and 3,

R3 to R11 are the same as or different from each other, and are each independently hydrogen; or an alkyl group having 1 to 10 carbon atoms, L12 and L14 are the same as or different from each other, and are each independently an alkylene group having 1 to 10 carbon atoms unsubstituted or substituted by an alkyl group, m1 is 1 or 2, and in the case where m1 is 2, two L12s are the same as or different from each other.

4. The (meth)acrylate compound of claim 2, wherein the hydroxyalkyl (meth)acrylate or the hydroxycycloalkyl (meth)acrylate is represented by the following Chemical Formula 4:

[Chemical Formula 4]

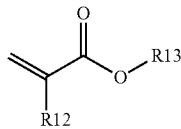

in Chemical Formula 4,

R12 is hydrogen; or an alkyl group having 1 to 10 carbon atoms, and

R13 is an alkyl group having 1 to 10 carbon atoms substituted by at least one hydroxy group (—OH); or a cycloalkyl group having 3 to 10 carbon atoms substituted by at least one hydroxy group (—OH).

5. The (meth)acrylate compound of claim 1, wherein Chemical Formula 1 is represented by the following Chemical Formula 1-1 or 1-2:

[Chemical Formula 1-1]

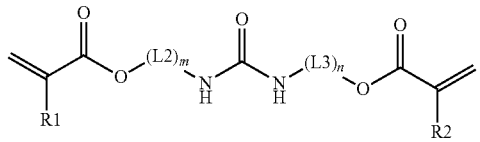

[Chemical Formula 1-2]

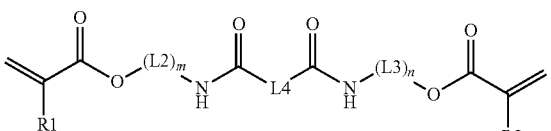

in Chemical Formulas 1-1 and 1-2,

L2 to L4 are the same as or different from each other, and are each independently an alkylene group having 1 to 10 carbon atoms unsubstituted or substituted by an alkyl group, in the case where L2 and L3 are the same as or different from each other and are each independently an unsubstituted alkylene group having 1 to 10 carbon atoms, one of R1 and R2 is an alkyl group having 1 to 10 carbon atoms, m and n are each 1 or 2, when m is 2, two L2s are the same as or different from each other, and when n is 2, two L3s are the same as or different from each other.

6. The (meth)acrylate compound of claim 1, wherein the (meth)acrylate compound is represented by any one of the following Chemical Formulas 1-3 to 1-5:

[Chemical Formula 1-3]

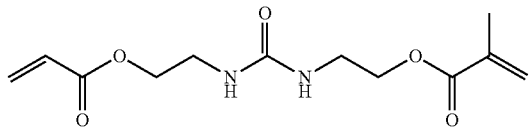

[Chemical Formula 1-4]

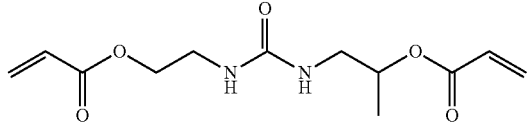

[Chemical Formula 1-5]

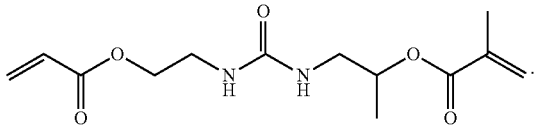

7. A copolymer comprising:
a repeating unit derived from the (meth)acrylate compound according to claim 1.

8. A homopolymer comprising:
a repeating unit derived from the (meth)acrylate compound according to claim 1.

9. The homopolymer of claim 8, wherein a glass transition temperature (Tg) of the homopolymer is 100° C. to 300° C.

10. The homopolymer of claim 8, wherein a storage modulus of the homopolymer measured by a DMA (dynamic mechanical analysis) method at 25° C. is 3000 to 30000 MPa.

11. The homopolymer of claim 8, wherein a gel fraction of the homopolymer is 85% to 100%.

12. The homopolymer of claim 8, wherein, of an IR spectrum of the homopolymer, a peak of a region band of 1408 cm$^{-1}$ which is a C=C band of a (meth)acrylate group of a repeating unit derived from the (meth)acrylate compound of the homopolymer is reduced as compared to a peak of an IR spectrum of the (meth)acrylate compound.

13. The homopolymer of claim 8, wherein, of an IR spectrum of the homopolymer, an integral value of peak areas of a region band of 1408 cm$^{-1}$ which is a C=C band of a (meth)acrylate group of a repeating unit derived from the (meth)acrylate compound of the homopolymer is reduced by 80% or more based on 100% of an integral value of peak areas of an IR spectrum of the (meth)acrylate compound.

\* \* \* \* \*